US00PP32099P2

(12) United States Plant Patent
Vijverberg

(10) Patent No.: US PP32,099 P2
(45) Date of Patent: Aug. 18, 2020

(54) ***DRACAENA* PLANT NAMED 'PVDRAGCI'**

(50) Latin Name: *Dracaena fragrans*
Varietal Denomination: PVDRAGCI

(71) Applicant: Fino Follaje S.A., San Jose (CR)

(72) Inventor: Piet Vijverberg, Monster (NL)

(73) Assignees: Fino Follaje S.A., Porton de Iberia (CR); Kwekerij Piet Vijverberg B.V., Monster (NL)

( * ) Notice: Subject to any disclaimer, the term of this patent is extended or adjusted under 35 U.S.C. 154(b) by 0 days.

(21) Appl. No.: 16/602,586

(22) Filed: Nov. 5, 2019

(51) Int. Cl.
*A01H 5/00* (2018.01)
*A01H 6/12* (2018.01)

(52) U.S. Cl.
USPC ..... Plt./383

(58) Field of Classification Search
USPC ..... Plt./383
CPC ..... A01H 5/00; A01H 6/12
See application file for complete search history.

*Primary Examiner* — Annette H Para
(74) *Attorney, Agent, or Firm* — Samuel R. McCoy, Jr.

(57) ABSTRACT

A new and distinct *Dracaena* plant named 'PVDRAGCI' which is characterized by the combination of an upright growth habit with variegated foliage borne atop a large cane, lorate-shaped and spiraled foliage, variegated foliage which is green and axially striped with a darker shade of green and broadly and irregularly margined light yellow, mature foliage which edged with a darker shade of yellow, and the stability of these characteristics from generation to generation.

4 Drawing Sheets

Latin name of the genus and species: The Latin name of the genus and species of the novel variety disclosed herein is *Dracaena fragrans.*

Variety denomination: The inventive cultivar of *Dracaena* disclosed herein has been given the variety denomination 'PVDRAGCI'.

BACKGROUND OF THE INVENTION

Parentage: 'PVDRAGCI' is a spontaneous whole-plant mutation of *Dracaena frangrans* 'Golden Coast' Plant Pat. No. 12,603 which was discovered at a commercial greenhouse in Monster, the Netherlands in 2018. The mutation was initially noted for its unique foliage variegation. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'PVDRAGCI' is accomplished by way of rooting large semi-hardwood stem cuttings, referred to as "canes". Propagation was first performed in 2018 at the inventor's commercial greenhouse in Monster, the Netherlands. Through one subsequent generation, the unique features of this cultivar have proven to be stable and true to type.

SUMMARY OF THE INVENTION

The cultivar 'PVDRAGCI' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PDVDRAGCI'. These characteristics in combination distinguish 'PVDRAGCI' as a new and distinct *Dracaena fragrans* cultivar:

1. *Dracaena* 'PVDRAGCI' exhibits an upright growth habit with upright foliage born atop a large cane; and
2. *Dracaena* 'PVDRAGCI' exhibits upright foliage near the apex, with foliage becoming progressively more relaxed, proximally; and
3. *Dracaena* 'PVDRAGCI' exhibits relatively large, lorate-shaped foliage which is moderately spiraled and curled downward, distally; and
4. *Dracaena* 'PVDRAGCI' exhibits medium green juvenile foliage which is axially striped with a darker shade of green, broadly and irregularly margined light yellow; and
5. *Dracaena* 'PVDRAGCI' exhibits green mature foliage which is broadly and irregularly margined yellow, and edged with a darker shade of yellow.

BOTANICAL DESCRIPTION OF THE PLANT

Figure 1:
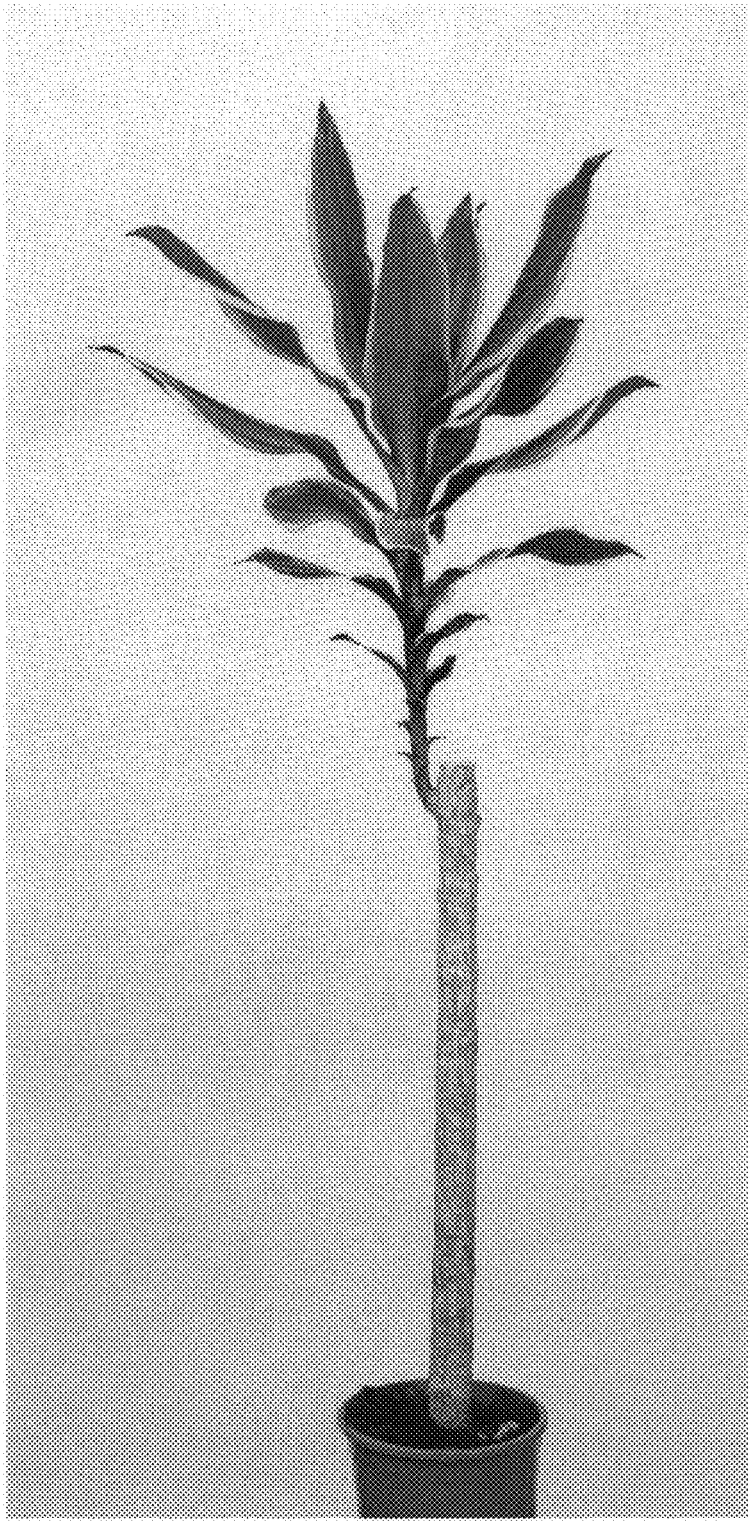
FIG. 1 illustrates, as nearly true as it is reasonably possible to make the same in color photographs of this type, an exemplary plant of 'PVDRAGCI' grown in Monster, the Netherlands. This plant, grown in a 15 cm nursery container, is approximately 18 weeks old from a rooted young plant.
Figure 2:
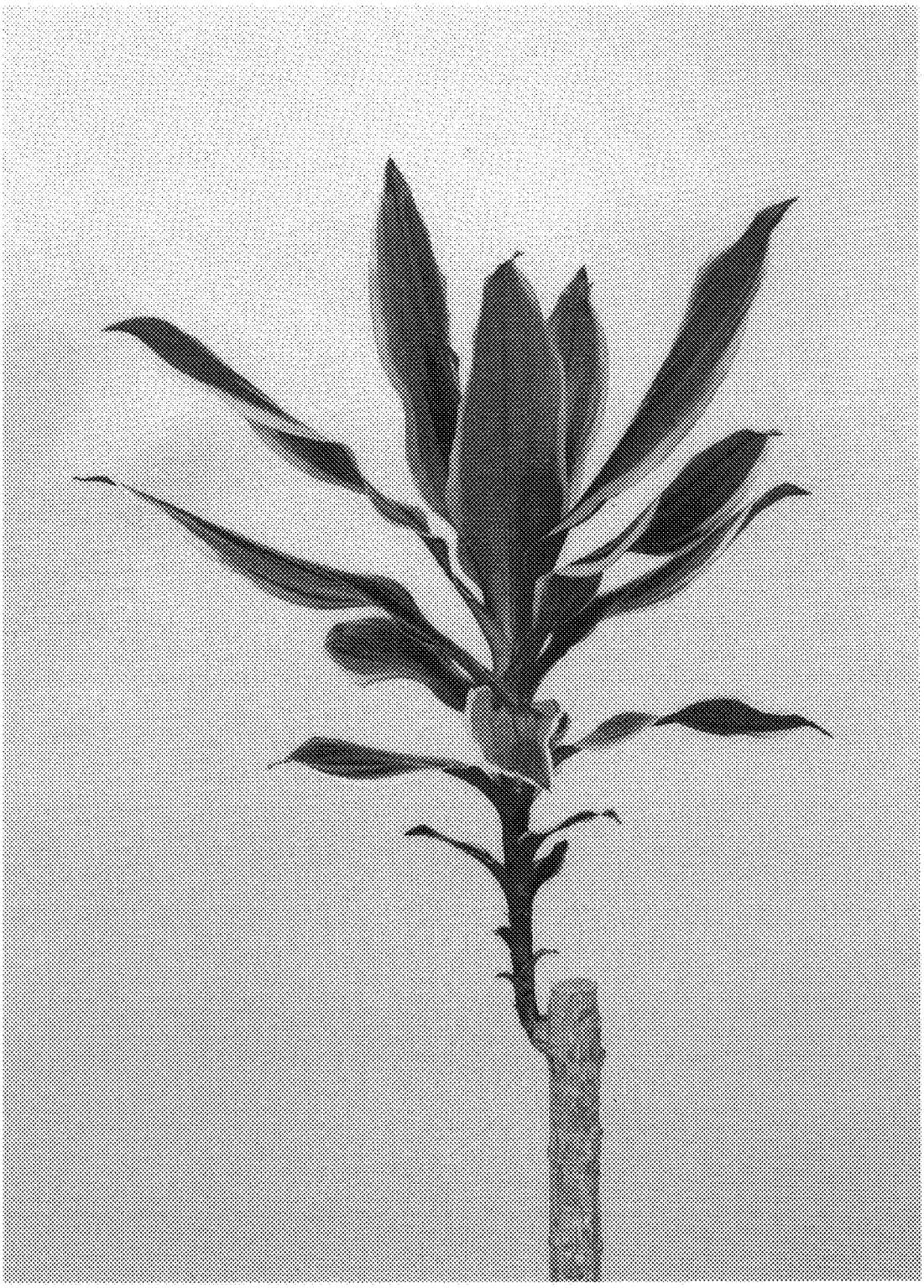
FIG. 2 illustrates, as nearly true as it is reasonably possible to make the same in color photographs of this type, the actively growing portion of an exemplary 'PVDRAGCI' plant.
Figure 3:
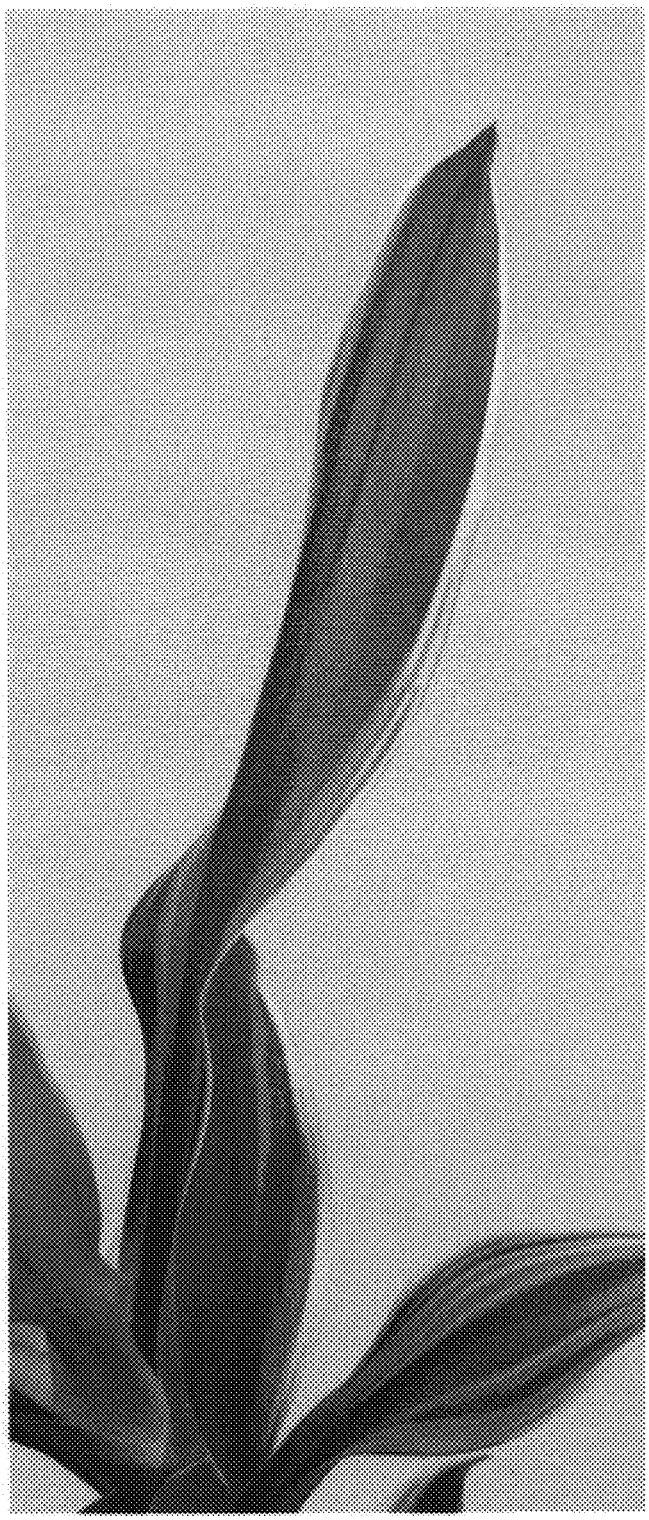
FIG. 3 illustrates, as nearly true as it is reasonably possible to make the same in color photographs of this type, the typical upper foliage of 'PVDRAGCI'.
Figure 4:
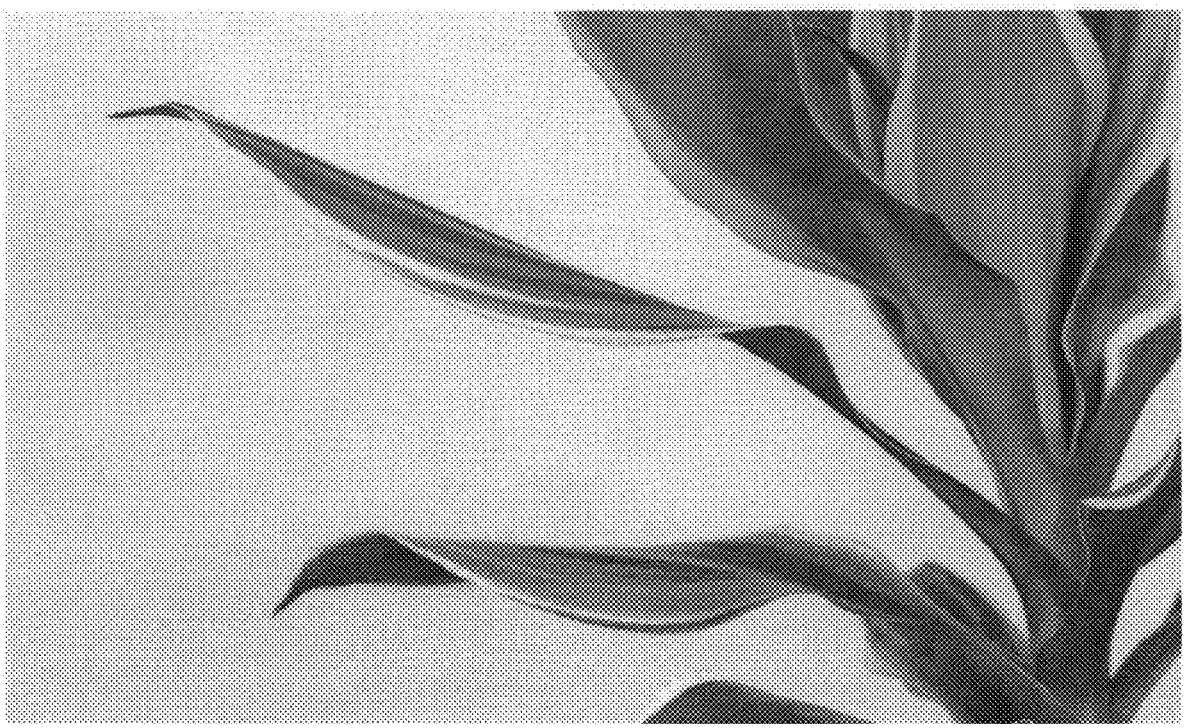
FIG. 4 illustrates, as nearly true as it is reasonably possible to make the same in color photographs of this type, the typical lower foliage of 'PVDRAGCI'.

The following observations and measurements, made in May of 2019, describe averages from a sample set of six specimens of 18 week-old 'PVDRAGCI' plants grown in 15 cm nursery pots in Monster, the Netherlands. Plants were produced using conventional greenhouse production protocols for *Dracaena* sp. which consisted of growing under shade cloth, irrigating at regular intervals with ebb and flow flood benches, and fertigation. No chemical treatments of any kind were utilized.

Those skilled in the art will appreciate that certain characteristics will vary with older or, conversely, with younger plants. 'PVDRAGCI' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'PVDRAGCI' and comparisons with the parent plant and most similar commercial *Dracaena* cultivar known to the inventor are provided below.

Plant description:

*Growth habit.*—Upright evergreen perennial with foliage born atop a cane.

*Plant profile.*—Obovate to broad elliptical.

*Average height from base to top of foliage.*—101.9 cm.

*Average width.*—Average of 46.0 cm.

*Growth rate.*—Moderately fast growing.

*Plant vigor.*—Moderately vigorous.

*Propagation details.*—Asexual propagation is accomplished by semi-hardwood stem cuttings.

*Time to initiate roots.*—Approximately 5 weeks are required to initiate roots at 25 degrees Celsius.

*Time to produce a marketable* 15 *cm potted plant.*—Approximately 15 to 30 weeks. Pinching will increase lateral branching.

*Disease and pest resistance or susceptibility.*—Neither tolerance nor resistance to normal diseases and pests of *Dracaena fragrans* have been observed.

*Environmental tolerances.*—Adapt to USDA Hardiness Zones 10 through 12 and temperatures as high as 40 degrees Celsius; moderate tolerance to rain and wind.

Root system:

*General.*—Fibrous; freely branched and moderately dense rooting.

*Distribution in the soil profile.*—Shallow to moderately deep.

*Texture.*—Smooth; glabrous.

*Color.*—Greyed-orange, RHS N 170A.

Stems:

*Branching characteristics.*—Not freely branched in nature; typically develops lateral branches only when manipulated by man by way of pruning. In cultivation, there is typically one lateral branch that arises from the cane.

*Quantity of main stems.*—1 cane.

*Quantity of lateral branches.*—1.

*Main stem.*—Attitude — Near vertical. Strength — Very strong. Texture — Glabrous; fissured. Color — Nearest to a mixture of greyed-orange and greyed-brown, RHS 165C and 199B.

*Lateral branches.*—Attitude — Near vertical. Strength — Very strong. Stem texture — Glabrous. Stem luster — Matte. Color, developing stems — Yellow-Green, nearest to RHS 144D. Color, mature stems — Yellow-Green, nearest to a mixture of RHS 144C and 144D. Color at the internodes — Yellow-Green, nearest to RHS 146B.

Foliage:

*Arrangement.*—Spiraled.

*Attachment.*—Sheathed.

*Division.*—Simple.

*Attitude.*—Foliage near the apex is upright to outward and becomes progressively more relaxed towards the cane.

*Number of leaves per lateral branch.*—17.

*Lamina.*—Dimensions — 28.3 cm long and 6.4 cm wide, on average. Shape — Lorate. Aspect — Moderately axially twisted (i.e. spiraled); distal portion on the lamina pointing downward. Apex — Acute with a short, soft but pointed tip. Base — Sheathed. Sheath Length — 2.4 cm. Width — 2.4 cm. Color, adaxial surface — Green-white, nearest to RHS 157A. Color, abaxial surface — Yellow-green, nearest to RHS 147B.

*Margin.*—Entire; coarsely undulate.

*Texture and luster of adaxial surface.*—Smooth, glabrous and moderately glossy.

*Texture and luster of abaxial surface.*—Smooth, glabrous and matte.

*Color.*—Juvenile foliage, adaxial surface — Yellow-green, nearest to RHS 144A; lightly axially striped with a darker shade of yellow-green, nearest to RHS 146B; margined yellow-green, nearest to RHS 150A. Juvenile foliage, abaxial surface — Nearest to in between green and yellow-green, RHS NN137B and 146A; broadly and irregularly margined yellow-green, nearest to RHS 144A, and edged yellow, nearest to RHS 11A. Mature foliage, adaxial surface — Nearest to in between green and yellow-green, RHS NN137B and 146A; broadly and irregularly margined yellow-green, nearest to RHS 144A, and edged yellow, nearest to RHS 11A. Mature foliage, abaxial surface — Green, nearest to a mixture of RHS 138A and 138B; irregularly margined yellow-green, nearest to RHS 146D, and edged yellow, nearest to a mixture of RHS 8A and 8B.

*Venation.*—Pattern — Parallel. Color, adaxial surface — Nearest to in between green and yellow-green, RHS NN137B and 146A; broadly and irregularly margined yellow-green, nearest to RHS 144A, and edged yellow, nearest to RHS 11A. Color, abaxial surface — The main vein, or midrib, is yellow-green, RHS 144B. All other veins are indistinguishable from the surrounding foliage: green, nearest to a mixture of RHS 138A and 138B, and irregularly margined yellow-green, nearest to RHS 146D, and edged yellow, nearest to a mixture of RHS 8A to 8B.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

Comparisons with the parent plant: Plants of the new cultivar 'PVDRAGCI' may be distinguished from its parent, *Dracaena fragrans* 'Golden Coast' Plant Pat. No. 12,603, by the characteristics described in Table 1.

TABLE 1

| Characteristic | 'PVDRAGCI' | 'Golden Coast' |
|---|---|---|
| Foliage size. | Larger and broader than 'Golden Coast'. | Smaller and narrower than 'PVDRAGCI'. |
| General coloration of the foliage margins. | Margined with a darker shade of yellow. | Margined with a lighter shade of yellow. |

Plants of the new cultivar 'PVDRAGCI' may be distinguished from the closest known commercial comparator, the common form of the species *Dracaena steudneri* (not patented), by the characteristics described in Table 2.

TABLE 2

| Characteristic | 'PVDRAGCI' | *Dracaena steudneri* |
|---|---|---|
| Foliage aspect. | More strongly spiraled (i.e. axially twisted) | Less spiralled. |
| Foliage attitude. | Lower foliage is more upright than those of Dracaena steudneri. | Lower foliage is more relaxed than those of 'PVDRAGCI'. |
| Internode length. | Longer internodes compared to Dracaena steudneri. | Shorter internodes compared to 'PVDRAGCI'. |
| Foliage size. | Larger than that of Dracaena steudneri. | Smaller than that of 'PVDRAGCI'. |
| General coloration of the foliage. | Variegated foliage comprised of dark green, medium green and light green axial striations, as well as yellow margins. | Has medium green leaves; no variegation. |

That which is claimed is:

1. A new and distinct cultivar of *Dracaena* plant named 'PVDRAGCI', substantially as described and illustrated herein.

* * * * *